United States Patent [19]

Yuasa et al.

[11] Patent Number: 4,587,057

[45] Date of Patent: May 6, 1986

[54] β-HYDROXYCYCLOPENTYLPEROXIDE COMPOUNDS AND THE USE THEREOF

[75] Inventors: Hitoshi Yuasa, Yokohama; Mitsuo Matsuno, Kawasaki; Hirosuke Imai, Yokohama, all of Japan

[73] Assignee: Nippon Oil Co., Ltd., Japan

[21] Appl. No.: 512,199

[22] Filed: Jul. 8, 1983

[30] Foreign Application Priority Data

Sep. 13, 1982 [JP] Japan .................. 57-159276
Jan. 7, 1983 [JP] Japan .................... 58-890
May 23, 1983 [JP] Japan ................. 58-90330

[51] Int. Cl.⁴ ............... C07C 179/18; C07C 179/06; C07C 179/02
[52] U.S. Cl. ..................... 260/453; 568/385; 568/485; 568/567; 568/903
[58] Field of Search ............... 568/560, 563, 564, 567, 568/568; 260/453 RZ

[56] References Cited

FOREIGN PATENT DOCUMENTS 148217 5/1981 German Democratic Rep. ............... 260/453 RZ

OTHER PUBLICATIONS

*Chemical Abstracts*, vol. 99, No. 157834s (1983).

*Primary Examiner*—Natalie Trousof
*Assistant Examiner*—Bruce D. Gray
*Attorney, Agent, or Firm*—Ostrolenk, Faber, Gerb & Soffen

[57] ABSTRACT

Novel peroxide compounds and the use thereof. In particular, the present invention concerns β-hydroxycyclopentylperoxide compounds of the general formula:

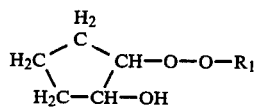

wherein $R_1$ represents hydrogen or an organic residue of 1 to 9 carbon atoms. These novel peroxide compounds are useful as an intermediate in the production of glutaraldehydes.

9 Claims, No Drawings

β-HYDROXYCYCLOPENTYLPEROXIDE COMPOUNDS AND THE USE THEREOF

FIELD OF THE INVENTION

The present invention relates to novel peroxide compounds and the use thereof. More particularly, the present invention relates to novel β-hydroxycyclopentylperoxide compounds and the use thereof, as an intermediate, in the production of glutaraldehydes.

BACKGROUND OF THE INVENTION

In the production of various chemical products, glutaraldehydes are important and useful as an intermediate starting material. Furthermore, they have many usages such as a tanning agent, a hardening agent for microcapsules, a germicide, a cross-linking agent, an enzyme fixer and the like.

Currently, glutaraldehydes are generally produced through a two-step reaction process which comprises a Diels-Alder reaction between acrolein and vinyl ether, and a hydrolysis of the resultant 2-alkoxy-dihydropyran. However, this process has drawbacks that the reaction time is too long, and that the starting materials are expensive and also are not easily available.

In addition to the above process, it is also well known to oxidize 1,5-pentanediols to produce the corresponding glutaraldehydes. However, this process suffers from the drawbacks such that the starting materials are expensive and the resulting glutaraldehydes have a very poor purity. Accordingly, the cost of the commercially available glutaraldehydes increases and is generally remarkably higher than that of other chemical products. It is therefore desirable to develop a production process of glutaraldehydes having a good purity from low-cost and easily, chemically synthesizable starting materials.

From these industrial viewpoints, it is expected to develop a production process of glutaraldehydes by using as a starting material cyclopentene or its derivatives which are industrially available at a relatively low cost. However, it has been already well-known that glutaraldehydes can be produced through oxidation of cyclopentene or its derivatives. Generally, this process comprises synthesizing 1,2-cyclopentane-diol from cyclopentene and then oxidizing the resulting 1,2-cyclopentane diol with an oxidizing agent such as lead tetraacetate or periodic acid. This process exhibits a good selectivity, but lead tetracetate and periodic acid used therein tend to be stoichiometrically consumed without additionally acting as a catalyst. Furthermore, it has been also well-known that cyclopentene is reacted with ozone to form the corresponding ozonide and the ozonide is then subjected to a reduction decomposition to produce glutaraldehydes. This process, however, is not suitable in an industrial production process of glutaraldehydes, since ozonide which is produced as an intermediate of the process has a risk of explosion.

Recently, a catalytic oxidation of cyclopentene or cyclopenteneoxide with hydrogen peroxide in the presence of molybdenum compounds is proposed in, for example, Japanese Patent Publication (Kokoku) Gazette Nos. 52-28606 and 51-33526. However, this catalytic oxidation process has important problems which must be solved.

A first problem of the catalytic oxidation process is that the reaction must be carried out in a non-aqueous system, since the reaction will be stopped if there is any water in the reaction system. This means that a commercially available aqueous solution of hydrogen peroxide at a low concentration is not suitable for use in this process and therefore it must be further extracted with an organic solvent to obtain water-free hydrogen peroxide. Further, in spite of use of water-free hydrogen peroxide, this process suffers from additional water problem. Namely, since water is produced during the reaction of cyclopentene or cyclopenteneoxide with hydrogen peroxide, it must be continuously removed from the reaction system.

A second problem of the process resides in that a plurality of 1,2-cyclopentanediols are produced as a by-product. It is therefore essential to reduce formation of such a by-product, since the by-product is difficult to separate from glutaraldehydes and therefore causes a reduction of the yield of the resulting glutaraldehydes.

A third problem of the process resides in that molybdenum compounds as the catalyst can be separated from the resulting glutaraldehydes with difficulty. This is because the molybdenum compounds are solubilized as a result of the reaction with hydrogen peroxide and an organic hydroperoxide. The solubilization of the molybdenum compounds is unavoidable, even if they are supported with a carrier material such as silica or alumina. Therefore, this process needs much effort for the purpose of recovering the catalyst.

The most important and fourth problem of the process resides in a further reaction of the resulting glutaraldehydes. Since glutaraldehydes are very unstable, they will be further oxidized to the corresponding carboxylic acids or they will be wastefully consumed in the accompanying condensation reaction, if the reaction is continued without separating the resulting glutaraldehydes from the reaction system.

Summarizing these problems, it is clear that the catalytic oxidation process described above does not ensure the production of glutaraldehydes having a high purity at an elevated yield. It is therefore considered that the production of glutaraldehydes in an industrial production scale can be attained with remarkable difficulty, when cyclopentene or cyclopenteneoxide is oxidized with hydrogen peroxide to produce glutaraldehydes.

In view of the above facts, it is generally concluded that, in the production of glutaraldehydes, their instability should be discussed in addition to ease of the practice of the process and yield of the resulting glutaraldehydes. For example, assuming that the proposed process for the production of glutaraldehydes can provide a higher yield, the process is considered to be insufficient for the industrial production purpose if it accompanies further reaction of the resulting glutaraldehydes and requires consumption of the energies for removing impurities.

Under these circumstances, we made efforts to find out a production process which enables effective production of glutaraldehydes which are important chemical starting materials, at a low cost, and completed the present invention which will be described hereinafter.

OBJECT OF THE INVENTION

It is an object of the present invention to provide novel β-hydroxycyclopentylperoxide compounds.

It is another object of the present invention to provide novel use of β-hydroxycyclopentylperoxide compounds, as an intermediate starting material, in the production of glutaraldehydes.

It is a still another object of the present invention to provide novel processes for the production of glutaraldehydes by using β-hydroxycyclopentylperoxide compounds as a starting material.

These and other objects and features of the present invention will become readily apparent from the following description of the invention.

SUMMARY OF THE INVENTION

According to the present invention, there is provided novel β-hydroxycyclopentylperoxide compounds of the general formula:

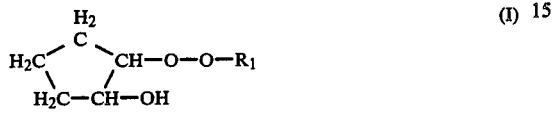

wherein $R_1$ represents hydrogen or an organic residue of 1 to 9 carbon atoms.

Also, according to the present invention, there is provided novel use of β-hydroxycyclopentylperoxide compounds, mentioned above, in the production of glutaraldehydes.

According to the present invention, said novel β-hydroxycyclopentylperoxide compounds can be utilized as the starting material for the production of glutaraldehydes, and can be effectively converted into glutaraldehydes by means of any one of the following procedures:

(a) thermal cracking,
(b) catalytic cracking, and
(c) hydrolysis of glutaraldehyde acetal which is a reaction product of said peroxide compound with alcohol.

DETAILED DESCRIPTION OF THE INVENTION

As previously described, novel β-hydroxycyclopentylperoxide compounds according to the present invention are represented by the general formula:

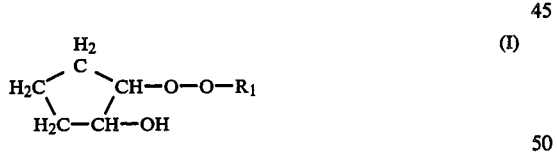

wherein $R_1$ represents hydrogen or an organic residue of 1 to 9 carbon atoms.

The organic residue $R_1$ for the formula (I) is preferably a hydrocarbon residue which may be optionally further substituted with a substituent such as =O, —OH or hydrogen.

Typical examples of β-hydroxycyclopentylperoxide compounds according to the present invention include:

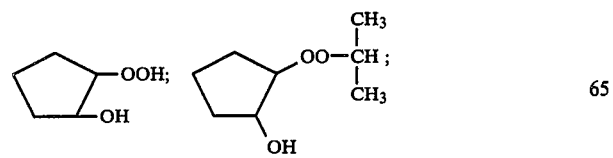

-continued

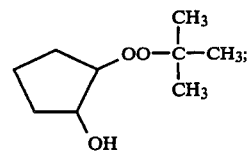

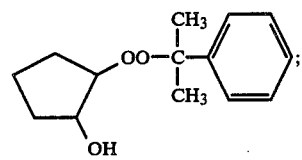

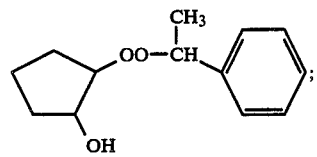

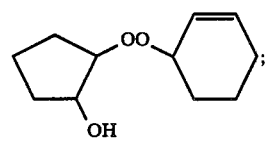

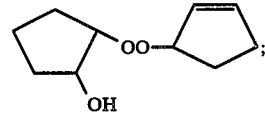

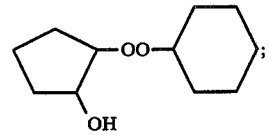

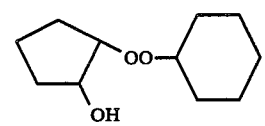

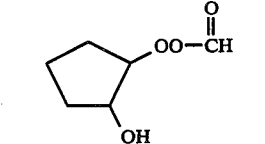

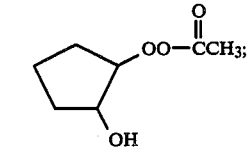

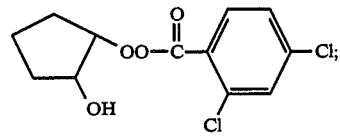

-continued

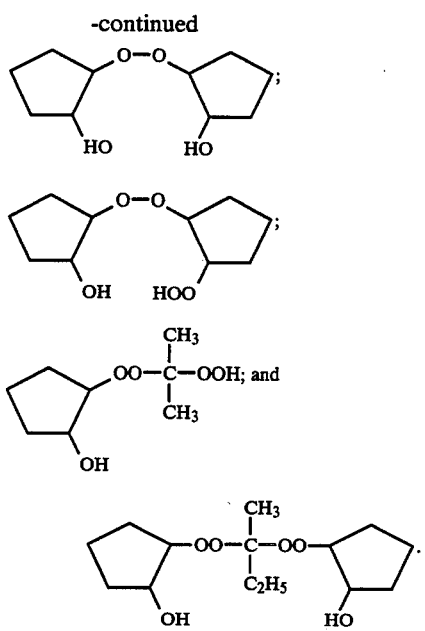

Beta-hydroxycyclopentylperoxide compounds of the present invention can be prepared by the reaction schema:

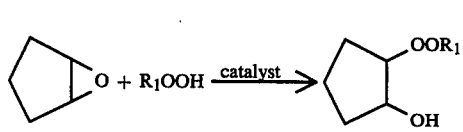
(A)

wherein $R_1$ is as defined above. As is shown in the reaction (A), they can be produced by reacting cyclopenteneoxide with hydrogen peroxide or an organic hydroperoxide in the presence of catalyst. Higher yields are obtained.

Alternatively, β-hydroxycyclopentylperoxide compound of the present can be prepared by the reaction:

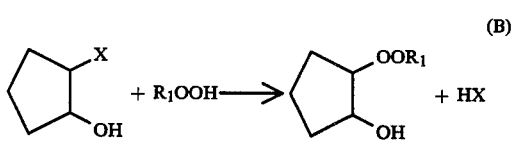
(B)

wherein:
X represents $OSO_3R'$, $OSO_2H$, $OSO_2R'$, $OCOR'$, Cl, Br, I, $ClO_4$, OH or OR',
R' represents an alkyl, cycloalkyl or aryl group of 1 to 16 carbon atoms, and
$R_1$ is as defined above.

As is apparent from the equation (B), they can be produced by reacting β-hydroxycyclopentane derivative with hydrogen peroxide or an organic hydroperoxide.

In the above-described production process (A) for β-hydroxycyclopentylperoxide compounds, useful catalysts include both of inorganic acids such as sulfuric acid, hydrochloric acid, phosphoric acid or the like, and organic acids such as acetic acid, trifluoroacetic acid, p-toluenesulfonic acid or the like. The catalysts useful in the process (A) further include an organic solid acids such as silica-alumina, acid clay or the like, and organic polymers containing acidic groups, for example, $SO_3H$ or COOH group, such as cation exchange resins. Furthermore, at least one element selected from the group consisting of boron, titanium, zirconium, vanadium, chromium, molybdenum and tungsten, and/or its compound may be used as the catalysts in the process (A).

A partial listing of useful representative catalysts for use in the process (A) include:

acids such as sulfuric acid, hydrochloric acid, phosphoric acid, acetic acid, trifluoroacetic acid and p-toluenesulfonic acid;

single metal substances such as titanium, zirconium, vanadium, chromium, molybdenum and tungsten;

oxides of boron, titanium, zirconium, vanadium, chromium, molybdenum and tungsten, for example, $H_3BO_3$, $HBO_2$, $B_2O_3$, $TiO_2$, $ZrO_2$, $VO_2$, $V_2O_5$, $CrO_2$, $Cr_2O_3$, $CrO_3$, $MoO_2$, $Mo_2O_5$, $MoO_3$, $WO_2$, $W_2O_5$, $WO_6$ or the like;

oxychlorides, fluorides, chlorides, bromides and iodides of said metal elements;

acid salts of said metal elements, for example, nitrate, pyrophosphate, polyphosphate, borate, carbonate, formate, acetate, propionate, butyrate, isobutyrate, caproate, laurate, stearate, oxalate, succinate, adipate benzoate, phthalate and benzenesulfonate;

acetylacetonate, phthalocyanine complexes of said metal elements;

carbonyl compounds of said metal elements, for example; $V(CO)_6$, $Cr(CO)_6$, $Mo(CO)_6$, $W(CO)_6$ or the like, and;

oxyacids such as molybdic acid, chromic acid, tungstic acid or the like, and the corresponding heteropolyacids as well as alkali metal or alkaline earth metal salts thereof.

The above-listed acids, single substances and compounds may be used separately or in combination. Further, one or more of them may be optionally supported on a carrier material such as alumina, silica, silica-alumina, zeolite and the like or organic polymeric substances. This can be carried out in accordance with the conventional manner.

As described previously, peroxide compounds are used as the starting material in the processes (A) and (B). They are represented by the general formula:

$R_1OOH$ in which $R_1$ is as defined above. Typical examples of the peroxide compounds used in the processes (A) and (B) include hydrogen peroxide,

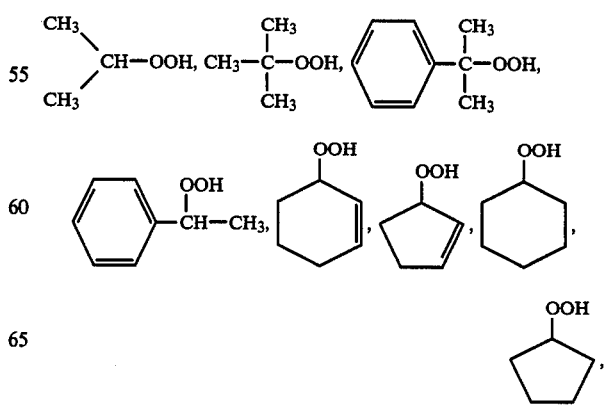

or the like. Among these peroxide compounds, we found that hydrogen peroxide and the compounds of 1 to 9 carbon atoms are most preferred.

The concentration of the peroxide compounds in the reaction solution may be varied within a relatively wide range. However, in order to avoid exotherm and runaway due to sudden reactions, it is desirable that the concentration is within the range of 1 to 50% by weight, preferably 3 to 40% by weight.

Furthermore, solvents are used in the practice of the processes (A) and (B). The solvents used herein include, for example, hydrocarbons of 3 to 16 carbon atoms, carboxylic acid esters containing an organic residue of 1 to 12 carbon atoms, phosphoric acid esters, sulfonic acid esters, carbonic acid amides, tertiary alcohols, ethers and the like.

Typical examples of the solvents used in the processes (A) and (B) include n-pentane, isopentane, cyclopentane, cyclopentene, n-hexane, isohexane, cyclohexane, octane, dodecane, benzene, toluene, xylene, ethyl benzene, ethyl acetate, butyl acetate, isoayml acetate, cyclohexyl acetate, butyl propionate, ethyl benzoate, dimethyl phthalate, diethyl phthalate, dimethyl formamide, dimethyl acetamide triethyl phosphate, trihexyl phosphate, trioctyl phosphate, dimethylmethane phosphonate, t-butyl alcohol, diethyl ether, anisole or the like.

In the practice of the above-described production processes (A) and (B), the reaction may be carried out in an aqueous or non-aqueous system. However, in order to avoid the formation of undesirable by-products such as 1,2-cyclopentanediols or the like, it is preferred to carry out the reaction in the non-aqueous system. In this connection, it is also preferred that hydrogen peroxide or an organic hydroperoxide used herein is dehydrated before the start of the reaction. In particular, hydrogen peroxide should be dehydrated before its use, since hydrogen peroxide is generally available in the form of its aqueous solution. Dehydration may be carried out in accordance with any conventional manners, for example, extraction of an aqueous hydrogen peroxide solution with organic solvent listed above, azeotropic distillation of the above solution to which said organic solvent is added, or vacuum distillation of the above solution. The dehydration process is also applicable to the dehydration of organic hydroperoxides, if they are in the form of an aqueous solution.

In the practice of the production processes (A) and (B), excessively higher or lower reaction temperature should be avoided, since the former results in a self-decomposition of the starting materials, namely, hydrogen peroxide or organic hydroperoxides, and the reaction products, namely, β-hydroxycyclopentylperoxides, while the latter is economically undesirable in view of the industrial production. Therefore, the reaction temperature in these processes is preferably within the range of −20° C. to 150° C. and particularly within the range of 0° C. to 100° C.

The reaction in the production processes (A) and (B) may be carried out in a batch process or a continuous process. The reaction time varies depending upon such factors as the reaction temperature and the composition of the reaction system, and is generally, at the most, ten hours.

Furthermore, in the practice of the above process (A), a ratio of hydrogen peroxide or organic hydroperoxide to cyclopenteneoxide may be varied within a wide range. However, excess use of hydrogen peroxide or organic hydroperoxide should be avoided, since it is economically undesirable and further it requires much effort in the recovering or after-treating process of the unreacted one. It is, therefore, preferred that the concentration of hydrogen peroxide or organic hydroperoxide is 0.05 to 3.0 moles, preferably 0.1 to 1.5 moles, per mole of cyclopenteneoxide.

The amount of the catalyst used in the process (A) may be varied within a wide range, depending upon its activity. Preferably, the catalyst may be used in an amount ranging from $10^{-7}$ to 0.05 moles catalyst and particularly from $10^{-5}$ to 0.01 moles catalyst per mole of cyclopenteneoxide.

Furthermore, as described previously, novel β-hydroxycyclopentylperoxide compounds of the present invention can be effectively used as the starting material for the production of glutaraldehydes. In production of glutaraldehydes, said β-hydroxycyclopentylperoxide compounds can be subjected to any one of the following reaction schema:

(a) β-hydroxycyclopentylperoxide $\xrightarrow{\text{thermal cracking}}$ glutaraldehyde;

(b) β-hydroxycyclopentylperoxide $\xrightarrow{\text{catalytic cracking}}$ glutaraldehyde, and;

(c) β-hydroxycyclopentylperoxide $\xrightarrow{\text{alcohol}}$ glutaraldehyde acetal $\xrightarrow{\text{hydrolysis}}$ glutaraldehyde.

In an aspect of the present invention, there is provided a novel process for the production of glutaraldehydes by thermally cracking β-hydroxycyclopentylperoxide compounds of the general formula:

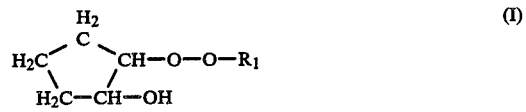

(I)

wherein $R_1$ is as defined above. (Hereinafter, this process will be referred to as "Thermal Cracking Process".)

The thermal cracking process of the present invention is characterized in that β-hydroxycyclopentylperoxide compounds capable of being easily and industrially derived from cyclopentene or cyclopenteneoxide can be used as the starting material, glutaraldehydes can be obtained at a high yield, and no 1,2-cyclopentanediols and other by-products are substantially produced. Further, the thermal cracking process is effective to prevent change of properties of the resulting glutaraldehydes, since it does not use acids, alkalis or metal catalysts which, if any, will cause said change of the properties. This is a merit of the use of thermal cracking. The thermal cracking process, in turn, prevents a condensation polymerization of the resulting glutaraldehydes or their oxidation into the corresponding carboxylic acids. As a result, the glutaraldehydes produced in the thermal cracking process of the present invention have a remarkably high purity and therefore can be easily purified. Furthermore, it should be noted that β-hydroxycyclopentylperoxide compounds used herein are more safe and have less risk of explosion in comparison with ozonide which is a reaction product of cyclopentene and ozone, and therefore are worthful as the starting material in view of the industrial use.

In the case of production of glutaraldehydes from cyclopentene or cyclopenteneoxide as the starting material, it is necessary to previously prepare β-hydroxycyclopentylperoxide compounds before start of the thermal cracking process of the present invention. Therefore, it is apparently conceived that a series of the production process from cyclopentene or cyclopenteneoxide to glutaraldehydes is complex and troublesome. But, this is overanxious. In fact, the production of glutaraldehydes according to the thermal cracking process of the present invention can be easily and satisfactorily attained in an industrial production scale. This surprising result is based on the fact that the synthesis and cracking of β-hydroxycyclopentylperoxide compounds can be attained with ease, and the products obtainable in each of the production steps show a high yield and can be refined with ease. In addition to this, the synthesis and cracking of β-hydroxycyclopentylperoxide compounds can be continuously carried out. Therefore, it is apparent from this that the actual process for the production of glutaraldehydes according to the present thermal cracking process is unexpectedly simple Further, the process for the production of glutaraldehydes according to the present thermal cracking process ensures the production of glutaraldehydes with high purity, which are able to be refined with ease, in contrast with the prior processes which comprise oxidation of cyclopentene or cyclopenteneoxide. This is because the present process includes the formation of relatively stable intermediates; β-hydroxycyclopentylperoxide compounds.

Furthermore, the production process according to the present thermal cracking process is free from the problem of the formation of the by-products such as cyclopentanediols. Assuming that cyclopentanediols are produced, they will be completely converted to β-hydroxycyclopentylperoxide compounds as a result of their reaction with hydrogen peroxide or organic hydroperoxide (The reaction will be described hereinafter). Since cyclopentanediols, when they are produced, are finally reusable as the starting material, the yield of the resulting glutaraldehydes increases remarkably and reaches about 100%.

Typical examples of β-hydroxycyclopentylperoxide compounds employed in the thermal cracking process of the present invention include:

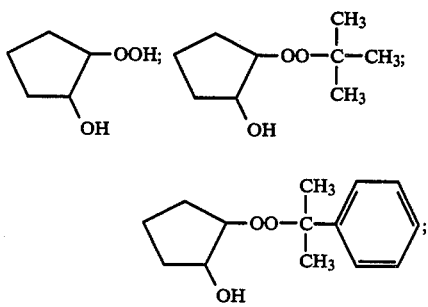

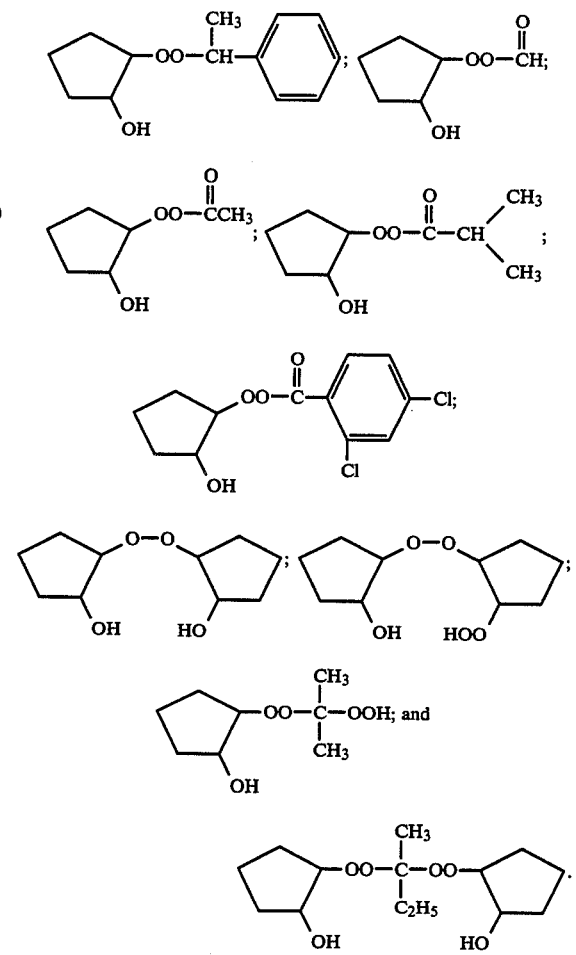

In the practice of the present thermal cracking process, the above-described β-hydroxycyclopentylperoxide compounds may be optionally used separately or in combination. The mixture of these cyclopentylperoxide compounds will be inoffensively cracked into glutaraldehydes.

The β-hydroxycyclopentylperoxide compounds, before thermal cracking, may be diluted with a suitable solvent or may be used without dilution. Further, they may be thermally cracked after vaporization. In all cases, the thermal cracking of the β-hydroxycyclopentylperoxide compounds should be gradually carfied out in order to avoid exotherm or runaway of the reaction.

When the β-hydroxycyclopentylperoxide compounds are intended to be cracked after dilution with solvent, any solvents may be used for the dilution purpose insofar as they do not react with the β-hydroxycyclopentylperoxide compounds and the resulting glutaraldehydes. The solvents used herein include, for example, hydrocarbons of 1 to 40 carbon atoms, esters and amides of carboxylic acids, phosphoric acids, phosphonic acids and sulfonic acids as well as ketones, alcohols, ethers and the like. They also include water. Useful solvents are hexane, dodecane, ethyl benzene, ethyl acetate, dimethyl phthalate, diethyl phthalate, trioctyl phosphate, methyl ethyl ketone, n-butyl alcohol, diethyl ether, anisole, water and the like.

In the thermal cracking of the β-hydroxycyclopentylperoxide compounds, the cracking temperature is preferably within the range of from 60° C. to 300° C. and particularly within the range of from 70° C. to 250° C. Excessively higher or lower cracking temperature is undesirable, since the former accompanies a polymerization of glutaraldehydes, while the latter results in an elongation of the reaction time. Further, the reaction or cracking time varies depending upon the concentration of the starting materials and the cracking temperature, and is generally very short. For example, the reaction time of five hours ensure a sufficient reaction.

The thermal cracking may be carried out in a batch process or a continuous process. Further, it should be preferably conducted slowly under heat exhausting conditions in order to remove heat produced in the cracking of the β-hydroxycyclopentylperoxide compounds.

In another aspect of the present invention, there is also provided a novel process for the production of glutaraldehydes by catalytically cracking β-hydroxycyclopentylperoxide compounds of the general formula (I) described above. (Hereinafter, this process will be referred to as "Catalytic Cracking Process".)

The production of glutaraldehydes according to the catalytic cracking process of the present invention may be conducted at a lower temperature, too. Since the reaction system is maintained at a lower temperature the resultant glutaraldehydes will be neither changed their properties nor consumed as a result of their undesirable condensation reaction. This indicates that the resultant glutaraldehydes show a remarkably high purity and are refined with ease. Further, the production process of this type can also provide similar merits as in the thermal cracking process described above. For example, the yield of the glutaraldehydes is as high as the thermal cracking process, and about 100%.

The catalytic cracking process of the present invention is carried out in the presence of catalyst. The catalysts employed in this catalytic cracking process are, for example, a single substance or compound of copper, silver, boron, aluminium, tin, lead, titanium, zirconium, vanadium, chromium, molybdenum, tungsten, manganese, iron, cobalt, nickel, ruthenium, rhodium, palladium, osmium, iridium and platinum as well as a mixture thereof. The catalyst compounds used herein may take any forms such as a complex of the metal element whose valency is zero or an inorganic or organic compound with different valencies. Examples of the catalyst compounds include oxides, mixed oxides, hydroxides, oxyacids, heteropolyacids and their salts and esters. These compounds may be derived, for example, inorganic hydroacids, oxyacids and organic carboxylic or sulfonic acids of less than 40 carbon atoms.

"Complex of the metal element", when used herein, means those which are generally referred to as an organic metal complex and contain coordinated organic and/or inorganic radicals Examples of representative catalysts for use in the catalytic cracking process of the present invention are as follows:

single metal substances such as copper, silver, aluminium, tin, lead, titanium, vanadium, chromium, molybdenum, tungsten, manganese, iron, cobalt, nickel, rhodium, palladium and platinum;

alloys such as copper-nickel, copper-platinum, copper-palladium, copper-gold, silver-platinum, silver-palladium, gold-platinum, cobalt-iridium, cobalt-palladium, cobalt-rhodium, cobalt-iron, nickel-palladium and nickel-iron;

oxides of copper, silver, boron, aluminium, tin, lead, titanium, vanadium, chromium, molybdenum, tungsten, manganese, iron, cobalt, nickel, rhodium, palladium, osmium, iridium and platinum, for example, $Cu_2O$, $CuO$, $Ag_2O$, $AgO$, $FeO$, $Fe_2O_3$, $Fe_3O_4$, $CoO$, $Co_3O_4$, $NiO$, $RuO_2$, $PdO$, $OsO_4$, $IrO_2$, $PtO_2$, $MnO_2$, $CrO_2$, $Cr_2O_3$, $CrO_3$, $MoO_2$, $Mo_2O_5$, $MoO_3$, $WO_2$, $W_2O_5$, $WO_6$, $VO_2$, $V_2O_5$, $ZrO_2$, $TiO_2$, $B_2O_3$, $Al_2O_3$, $PbO$ or the like;

oxychlorides, fluorides, chlorides, bromides and iodides of said metal elements;

acid salts of said metal elements, for example, inorganic acid salts such as nitrate, sulfate, phosphate or the like, organic acid salts such as pyrophosphate, polyphosphate, borate, carbonate, formate, acetate, propionate, butyrate, isobutyrate, caproate caprylate, laurate, naphthenate stearate, oxalate, succinate, glutarate adipate, benzoate, phthalate or the like, and benzenesulfonate;

acetylacetonate, phthalocyanine complexes of said metal elements;

carbonyl compounds of said metal elements, for example, $V(CO)_6$, $Cr(CO)_6$, $Mo(CO)_6$, $W(CO)_6$, $Fe(CO)_5$, $Ni(CO)_4$, $Ru_3(CO)_{12}$, $Os_3(CO_{12}$ or the like; and oxyacids such as molybdic acid, chromic acid, osmic acid, tungstic acid or the like, and the corresponding heteropolyacids as well as alkali metal or alkaline earth metal salts thereof.

If desired, a mixture of one or more single substances and compounds mentioned above may be used without hindrance. Further, the above-listed catalysts may be supported on a suitable carrier such as alumina, silica, silica-alumina, zeolite and the like or optionally organic polymeric substances, in accordance with the conventional manners.

Before start of the catalytic cracking process of the present invention, the starting β-hydroxycyclopentylperoxide compounds may be diluted or may not be diluted with a suitable solvent. Optionally, they may be evaporated and then introduced into a catalyst layer of the reactor for cracking purposes. Anyway, the reaction in the catalytic cracking process of the present invention should be gradually proceeded in order to prevent an exothermic reaction or runaway of the reaction.

When the starting β-hydroxycyclopentylperoxide compounds are diluted with solvent before their catalytic cracking, any solvents may be employed as an diluent insofar as they do not react with the β-hydroxycyclopentylperoxide compounds and the resulting glutaraldehydes. The solvents used herein include, for example, hydrocarbons of 1 to 40 carbon atoms, esters and amides of carboxylic acids, phosphoric acids, phosphonic acids and sulfonic acids, ethers and the like. They also include water. Typical examples of the solvents are hexane, nonane, dodecane, benzene, ethyl acetate, isoamyl acetate, dimethyl phthalate, diethyl phthalate, trioctyl phosphate, dibutyl ether, anisole, water and the like.

In the practice of the catalytic cracking process of the present invention, the concentration of the starting β-hydroxycyclopentylperoxide compound in the reaction solution is preferably within the range of 1 to 50% by weight and particularly within the range of 1 to 25% by weight. This concentration range is effective to prevent an exothermic reaction or runaway of the reaction due to sudden reactions.

The concentration of the catalysts employed in the catalytic cracking process varies widely with a useful concentration range being $10^{-6}$ to $10^{-1}$ moles catalyst per mole of β-hydroxycyclopentylperoxide. A most preferred concentration range is from $10^{-5}$ moles to $10^{-1}$ moles per mole of β-hydroxycyclopentylperoxide. If the concentration of the catalyst exceeds the upper limit of the above range, the velocity of reaction will increase with the rise of costs of the catalyst. In contrast, if the concentration of the catalyst is less than lower limit of the above range, the velocity of reaction will decrease remarkably.

In the practice of the catalytic cracking process, higher reaction temperature should be avoided in order to prevent polymerization of the resulting glutaraldehydes. Further, excessively lower reaction temperature should be also avoided, since it causes decrease of the reaction velocity. Therefore, it is desirable that the catalytic cracking process is carried out within the temperature range of 0° to 200° C., preperably 10° to 100° C.

The reaction time in the catalytic cracking process of the present invention varies depending upon the reaction temperature and the composition of the reaction system, and is generally very short. For example, satisfactory reaction can be attained within the reaction time of five hours.

The catalytic cracking process of the present invention may be carried out in a batch process or a continuous process. Further, cracking in this process is preferably carried out gradually under heat exhausting conditions in order to remove heat produced during the cracking.

In a still another aspect of the present invention, there is also provided a novel process for the production of glutaraldehydes via glutaraldehyde acetal. The process (this will be referred hereinafter to as "Acetal Process") comprises reacting β-hydroxycyclopentylperoxide compounds of the general formula (I), described above, with alcohol and then hydrolyzing the resulting glutaraldehyde acetal to produce glutaraldehydes.

As described above, we studied the synthesis of glutaraldehydes from β-hydroxycyclopentylperoxide compounds which contain as a skeleton the structure:

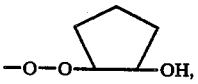

and now completed its invention. During this study, we also found the fact that said compound containing the structure:

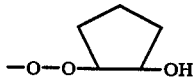

can be converted to acetal compounds, if they are reacted with alcohols in the presence of certain metal catalysts. In other words, we found the following reaction schema:

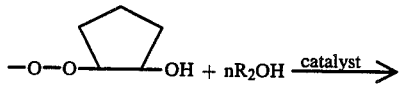

-continued $$x(R_2O)_2CH(CH_2)_3CH(OR_2)_2 + y(R_2O)_2CH(CH_2)_3CHO +$$

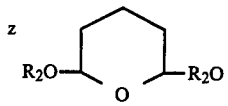

wherein:
$R_2$ represents an organic, straight chain or branched chain, aliphatic or alicyclic group of 1 to 12 carbon atoms, and x, y, z and n is an integer, with the proviso that $4x+2y+2z=n$ and $n\leq 4$. The above reaction is novel and is a basis of the invention of the acetal process.

We found that, when the acetal process of the present invention is utilized in the production of glutaraldehydes, the production can be conducted safely and the glutaraldehydes having a high purity can be obtained. Namely, when unstable β-hydroxycyclopentylperoxide compounds produced from cyclopentene or cyclopenteneoxide are catalytically decomposed in a stoichiometric or more amounts of alcohol to convert them into stable acetal compounds, a runaway of the reaction and a risk of the explosion can be completely removed. In addition to this, since the resulting acetal compounds are thermally stable, they can be easily subjected to a refining process such as distillation to remove undesired by-products, for example, cyclopentanediols and oligomers, thereby resulting in a glutaraldehyde precursor with a high purity. Furthermore, the acetal compounds are chemically stable, and therefore can be stored for a long period without causing any change of properties, insofar as the mix of acids and/or water is avoided.

The resulting acetal compounds are then hydrolyzed in accordance with the conventional manner in order to distill off by-product alcohols. Finally, an aqueous solution of high purity glutaraldehydes is obtained.

The acetal compounds produced in the acetal process of the present invention have the general formulae:

$$X-(CH_2)_3-Y \qquad (II)$$

wherein:
X and Y each represents

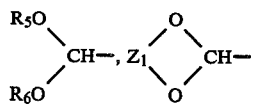

or a formyl group,
$R_5$ and $R_6$ each represents $R_2$ or $HOZ_1$,
$Z_1$ represents an organic, straight chain or branched chain, aliphatic or alicyclic group of 2 to 12 carbon atoms, and
$R_2$ is as defined above, with the proviso that X and Y may be the same except for X=Y=formyl, and;

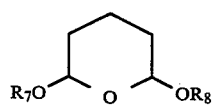

(III)

wherein $R_7$ and $R_8$ each represents $R_2$ or $HOZ_1$ in which $R_2$ and $Z_1$ are as defined above.

Typical examples of the resulting acetal compounds are:

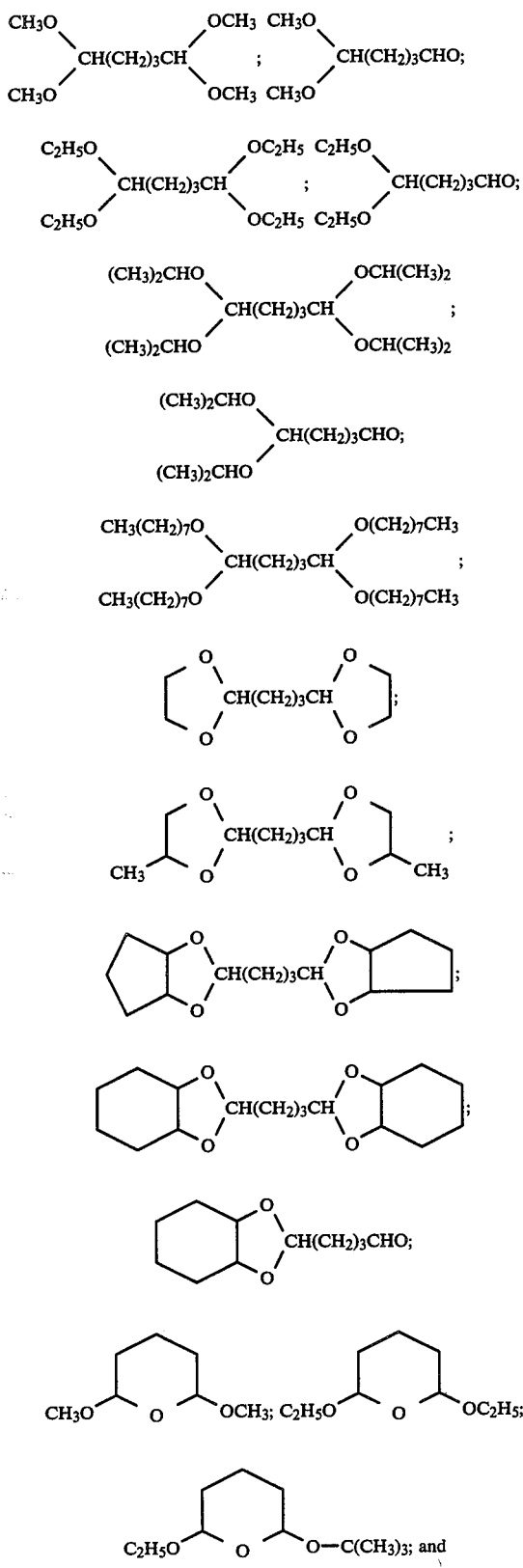

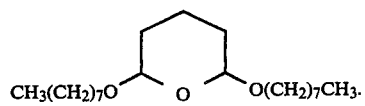

Under certain reaction conditions, two or more of these acetal compounds will be concurrently produced. However, they are easily separated from each other through conventional rectification processes, or they are hydrolyzed to form glutaraldehydes.

As described above, the acetal process of the present invention is carried out in the presence of catalyst. The catalysts employed in this process are, for example, a single substance or compound of copper, silver, boron, aluminium, tin, lead, titanium, zirconium, vanadium, chromium, molybdenum, tungsten, manganese, iron, cobalt, nickel, ruthenium, rhodium, palladium, osmium, iridium and platinum as well as a mixture thereof. The catalyst compounds used herein may take any forms such as a complex of the metal element whose valency is zero or an inorganic or organic compound with different valencies.

Examples of the catalyst compounds include oxides, mixed oxides, hydroxides, oxyacids, heteropolyacids and their salts and esters. These compounds may be derived, for example, inorganic hydroacids, oxyacids and organic carboxylic or sulfonic acids of less than 40 carbon atoms.

"Complex of the metal element", as defined above, means those which are generally referred to as an organic metal complex and contain coordinated organic and/or inorganic radicals.

Examples of representative catalyst for use in the acetal process of the present invention are as follows:

single metal substances such as copper, silver, aluminium, tin, lead, titanium, vanadium, chromium, molybdenum, tungsten, manganese, iron cobalt, nickel, rhodium, palladium and platinum;

alloys such as copper-nickel, copper-platinum, copper-palladium, copper-gold, silver-platinum, silver-palladium, gold-platinum, cobalt-iridium, cobalt-palladium, cobalt-rhodium, cobalt-iron, nickel-palladium and nickel-iron;

oxides of copper, silver, boron, aluminium, tin, lead, titanium, vanadium, chromium, molybdenum, tungsten, manganese, iron, cobalt, nickel, rhodium, palladium, osmium, iridium and platinum, for example, $Cu_2O$, $CuO$, $Ag_2O$, $AgO$, $FeO$, $Fe_2O_3$, $Fe_3O_4$, $CaO$, $Co_3O_4$, $NiO$, $RuO_2$, $PdO$, $OsO_4$, $IrO_2$, $PtO_2$, $MnO_2$, $CrO_2$, $Cr_2O_3$, $CrO_3$, $MoO_2$, $Mo_2O_5$, $MoO_3$, $WO_2$, $W_2O_5$, $WO_6$, $VO_2$, $V_2O_5$, $ZrO_2$, $TiO_2$, $B_2O_3$, $Al_2O_3$, $PbO$ or the like;

oxychlorides, fluorides, chlorides, bromides and iodides of said metal elements;

acid salts of said metal elements, for example, inorganic acid salts such as nitrate, sulfate, phosphate or the like, organic acid salts such as pyrophosphate, polyphosphate, borate, carbonate, formate, acetate, propionate, butyrate, isobutyrate, caproate caprylate, laurate, naphthenate stearate, oxalate, succinate, glutarate, adipate, benzoate, phthalate or the like, and benzenesulfonate;

acetylacetonate, phthalocyanine complexes of said metal elements;

carbonyl compounds of said metal elements, for example, V(CO)$_6$, Cr(CO)$_6$, Mo(CO)$_6$, W(CO)$_6$, Fe(CO)$_5$, Ni(CO)$_4$, Ru$_3$(CO)$_{12}$, Os$_3$(CO)$_{12}$ or the like, and;

oxyacids such as molybdic acid, chromic acid, osmic acid, tungstic acid or the like, and the corresponding heteropolyacids as well as alkali metal or alkaline earth metal salts thereof.

If desired, a mixture of one or more single substances and compounds mentioned above may be used without hindrance. Further, the above-listed catalysts may be supported on a suitable carrier such as alumina, silica, silica-alumina, zeolite and the like or optionally organic polymeric substances, in accordance with the conventional manners.

The starting β-hydroxycyclopentylperoxide compounds employed in the acetal process of the present invention are the same as those exemplified above, for example, with respect to the practice of the thermal cracking process of the present invention. In this process, the starting cyclopentylperoxide compounds may be used separately or in combination. The use of a mixture of these starting compounds, of course, causes no problems and difficulties.

The alcohols employed in the acetal process of the present invention include a monohydric alcohol of the general formula:

R$_2$OH wherein R$_2$ is as defined above, or a polyhydric alcohol of the general formula:

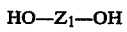

HO—Z$_1$—OH wherein Z$_1$ is as defined above. Carbon atom(s) on Z$_1$ of the above formula may contain 1 to 4 hydroxyl groups bonded thereto, with the proviso that two or more hydroxyl groups should not be bonded to the same carbon atom on Z$_1$. These alcohols may be used separately or in combination.

Typical examples of useful alcohol include nethanol, ethanol, n-propyl alcohol, isopropyl alcohol, n-butyl alcohol, sec.-butyl alcohol, n-amyl alcohol, isoamyl alcohol, n-hexanol, octanol, dodecanol, cyclopentanol, cyclohexanol, cyclododecanol, ethylene glycol, propylene glycol, 1,5-pentanediol, 1,2-hexanediol, glycerol, 1,2-cyclopentanediol, 1,2-cyclohexanediol, 1,3-cyclododecanediol and the like Before carrying out the acetal process of the present invention, the starting β-hydroxycyclopentylperoxide compounds may be dissolved in any of the above-listed alcohols, or they may be dissolved in a suitable solvent other than the above alcohols. Any solvents may be utilized for this purpose, insofar as they do not react with the starting β-hydroxycyclopentylperoxide compounds and the resulting acetal compounds. Useful solvents are, for example, hydrocarbons of 5 to 12 carbon atoms, esters of carboxylic acids, phosphoric acids and sulfonic acids each of which esters contains an organic group of 1 to 12 carbon atoms, carboxylic acid amides, ethers and the like.

Typical examples of the useful solvent include n-pentane, n-hexane, dodecane, ethyl benzoate, dimethyl phthalate and the like.

In the practice of the acetal process of the present invention, the concentration of the starting β-hydroxycyclopentylperoxide compounds in the reaction solution is preferably within the range of 0.1 to 50% by weight and particularly within the range of 0.5 to 20% by weight. This concentration range is effective to prevent an exothermic reaction or runaway of the reaction due to sudden reactions.

The amount of the alcohols used herein depends on the concentration conditions of the starting cyclopentylperoxide compounds, and is therefore determined within the range satisfying such concentration conditions. Generally, it is preferred to use 4 moles or more of the alcohols per mole of the starting cyclopentylperoxide compounds. Further, when the maximum amount of the alcohols is included within the above-described concentration range of the starting cyclopentylperoxide compounds, such a maximum amount is acceptable.

The concentration of the catalysts employed in the acetal process varies widely depending upon their activity with a useful concentration range being $10^{-6}$ to $10^{-1}$ moles catalyst per mole of β-hydroxycyclopentylperoxide. A most preferred concentration range is from $10^{-5}$ moles to $10^{-1}$ moles per mole of β-hydroxycyclopentylperoxide.

In the practice of the acetal process, such higher temperature that the starting β-hydroxycyclopentylperoxide compounds are non-catalytically but thermally cracked and therefore undesirable by-products are produced, and an excessively lower temperature which will cause a decrease of the reaction velocity should be avoided. It is, therefore, desirable to conduct the acetal process at a temperature ranging from 0° C. to 200° C., particularly at a temperature lower than the boiling point of the alcohols used.

The acetal process may be carried out in a batch system or in a continuous system. The reaction time in these systems varies depending upon the reaction temperature and the composition of the reaction system, and is generally less than 10 hours.

The following examples are provided to further illustrate the present invention and to aid in the understanding of the present invention.

EXAMPLE 1

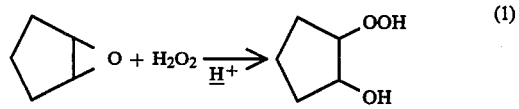
(1)

In a 200 cc, glass reactor fitted with a stirrer, a reflux condenser and a dropping funnel were charged 3 g of Amberlist 15 (strong acid, cation exchange resin; the trade name of Roam & Haas Co.) and 20 g of dimethyl phthalate. The temperature in the reactor was elevated to 30° C. and, with stirring, a solution of 16.8 g of cyclopenteneoxide, 7.5 g of anhydrous hydrogen peroxide and 30 g of dimethyl phthalate was dropwise added through the funnel for one hour.

After the addition was completed, the reaction was further continued at 30° C. for 3 hours, and then the catalyst was filtered off. The resulting solution of dimethyl phthalate was liquid chromatographed on silica gel eluting with benzene/ethanol (20:1). This gave 20 g of product as a colorless, viscous liquid.

Elemental Analysis: C 50.79 wt. %; 0 40.73 wt. %; H 8.48 wt. %

It is apparent from this that the product has the experimental or composition formula: C$_5$H$_{10.02}$O$_{3.01}$. Further, the molecular weight of the product, when determined in a methanol solution of the product by means of a vapor pressure osmometer, is 117. Accordingly, the molecular formula of the product is conceived to be $C_5H_{10}O_3$. Furthermore, the iodometry indicates that the product contains 8.5 meq. of peroxy group per gram. 'H-NMR spectral analysis of the product shows the following absorption data:

hydroperoxy proton ($\delta=10.6$ ppm);
hydroxy proton, $\alpha$-methine proton of hydroxy and $\alpha$-methine proton ($\delta=4.3$ ppm);
functional group-free methylene proton of cyclopentane ring ($\kappa=1.7$ ppm), and;
area ratio=1:3:6.

C-NMR spectral analysis of the product shows the following absorption data:

5 carbon of cyclopentane ring (five lines);
E-carbon of hydroxy ($\delta=76.1$ ppm), and;
3 carbons of methine ($\delta=22.6\sim33.5$ ppm, triplet).

From these analytical data, the product is identified to be $\beta$-hydroxycyclopentylhydroperoxide.

EXAMPLE 2

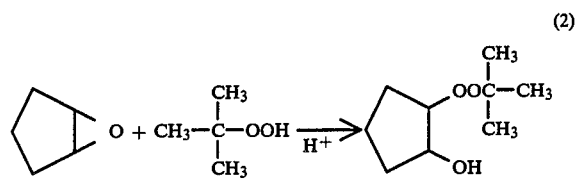

(2)

In a 500 cc, glass reactor fitted with a stirrer, a reflux condenser and a dropping funnel were charged 15 g of Amberlist 15 and 100 g of benzene. Thereafter, the temperature in the reactor was elevated to 40° C. and, with stirring, a solution of 8.5 g of cyclopenteneoxide, 105 g of t-butyl hydroperoxide and 220 g of benzene was dropwise added through the funnel for 30 minutes.

After the addition was completed, the reaction was continued for further 5 hours at 40° C., and then the catalyst was filtered off. The reaction solution was vacuum distilled to yield 115 g of product as a colorless liquid, boiling point (b.p.) 49° C. at 0.7 mmHg.

Elemental Analysis: C 62.01 wt. %; 0 27.59 wt. %; H 10.40 wt %

It is apparent from this that the product has the experimental or composition formula: $C_9H_{18.11}O_{3.03}$. Further, the molecular weight of the product, when determined in a benzene solution of the product by means of a vapor pressure osmometer, is 175. Accordingly, the molecular formula of the product is conceived to be $C_9H_{18}O_3$. Furthermore, $^1$H-NMR spectral analysis of the product shows the following absorption data:

$\delta=4.1\sim4.3$ ppm: hydroxy proton ($\delta=4.2$ ppm) and $\alpha$-methine proton of hydroperoxy ($\delta=4.1$ ppm);
$\alpha$-methine proton of hydroxy ($\delta=3.6$ ppm);
methylene proton of cyclopentanering ($\delta=1.7$ ppm);
methyl proton of t-butyl ($\delta=1.2$ ppm), and;
area ratio=2:1:6:9.

C=NMR spectral analysis of the product shows the following absorption data:

$\alpha$-carbon of t-butyl peroxy ($\delta=90.9$ ppm);
$\alpha$-carbon of hydroxy ($\delta=75.8$ ppm);
3-carbons of methylene of cyclopentanering ($\delta=32.7$, 28.4 and 21.8 ppm); carbon bonded to oxygen of t-butyl peroxy ($\delta=79.6$ ppm), and;
3 carbons of methyl ($\delta=26.5$ ppm).

From these analytical data, the product is identified to be $\beta$-hydroxycyclopentyl-t-butylperoxide.

EXAMPLE 3

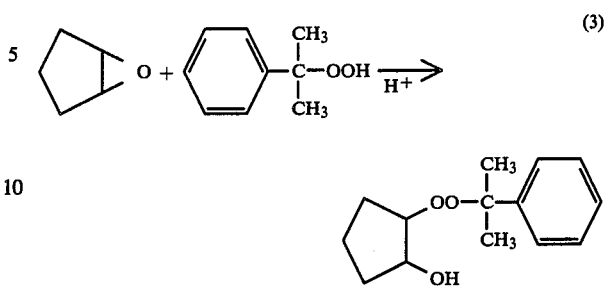

(3)

Beta-hydroxycyclopentylcumylperoxide (3) was prepared similarly as in Examples 1 and 2: In a 500 cc reactor were placed 13 g of Amberlist 15 and 100 g of dimethyl phthalete. Then, at 30° C., a solution of 87 g of cyclopenteneoxide, 150 g of cumene hydroperoxide and 80 g of dimethyl phthalate was dropwise added for 30 minutes.

After the addition was completed, the reaction was conducted for 7 hours at 30° C., and the catalyst was filtered off. The dimethyl phthalate solution was liquid chromatographed on silica gel eluting with benzene/ethanol (20:1). This gave 165 g of product as a viscous liquid.

Elemental Analysis: C 71.01 wt. %; 0 20.45 wt. %; H 8.54 wt. %

It is apparent from this that the product has the experimental or composition formula: $C_{14}H_{20.02}O_{3.02}$. Further, the molecular weight of the product, when determined in a benzene solution of the product by means of a vapor pressure osmometer, is 235. Accordingly, the molecular formula of the product is $C_{14}H_{20}O_3$.

The iodometry indicates that the product contains 4.23 meq. of peroxy group per gram. The amount of peroxide per mole of product, when calculated from the molecular weight of the product (235) and said iodometric data (4.23 meq/g of peroxy group), is 0.998 gram equivalent. This means that a molecule of the contains one peroxy group.

'H-NMR spectral analysis of the product shows the following absorption data:

proton of benzene ring ($\delta=8.3$ ppm);
hydroxy proton and each E-methine proton of peroxy ($\delta=4.0\sim4.3$ ppm); $\alpha$-proton of hydroxy ($\delta=3.6$ ppm);
methyl proton of cumyl and methlyene proton of cyclopentane ring ($\delta=1.3\sim2.2$), and;
area ratio=5:2:1:12.

Further, IR analysis indicates a characteristic absorption of 3640 cm$^{-1}$ and phenyl-inherent, characteristic absorptions at 3125, 3110 and 3090 cm$^{-1}$.

From these analytical data, the product is identified to be $\beta$-hydroxycyclopentylcumylperoxide. Correctness of this identification will be further certified in the catalytic cracking process of the product which is described hereinafter (In addition to acetone and phenol, glutaraldehydes were produced as a result of catalytic cracking of the product). Catalytic cracking of $\beta$-hydroxycyclopentylcumylperoxide [(3) in the above reaction equation]

In a 100 cc, glass reactor fitted with a stirrer, a reflux condenser and a dropping funnel were placed 0.2 g of palladium black and 50 g of dimethyl phthalate. The temperature in the reactor was then elevated to 70° C., and, with stirring, 24 g of β-hydroxycyclopentylcumyl-peroxide (3) was added through the dropping funnel for one hour.

After the addition was completed, heating and stirring were further continued for 3 hours at 70° C. The product was gas chromatographed. This showed that 8 g of glutaraldehydes were produced in this process. Further, the cracking solution was tested with the iodometry to check the remaining peroxide in the solution. No peroxide was detected.

EXAMPLE 4

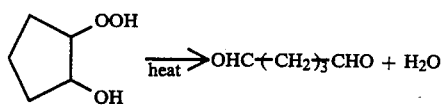

A dimethyl phthalate solution of β-hydrox,ycyclopentylhydroperoxide (1) prepared as in Example 1 was thermally cracked as follows:

In a 200 cc, glass reactor fitted with a stirrer, a reflux condenser and a dropping funnel was placed 20 g of dimethyl phthalate. The temperature was then elevated to 150° C., and, with stirring, 70 g of a dimethyl phthalate solution containing 20.7 g of β-hydroxycyclopentyl-hydroperoxide (1) was dropwise added through the funnel for 2 hours.

After the addition was completed, heating and stirring were continued for one hour, and the reaction solution was gas chromatographed on the column of FFAP (free fatty acid polyester). It was found that the reaction solution contains 26% by weight of glutaraldehydes. No remaining peroxide in the reaction solution was confirmed by the iodometry. The reaction solution was then extracted with water to separate glutaraldehydes. Yield 15.1 g.

EXAMPLE 5

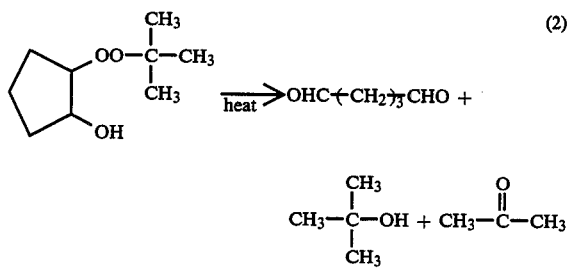

Beta-hydroxycyclopentyl-t-butylperoxide (2) prepared as in Example 2 was thermally cracked as follows:

In a 200 cc, glass reactor fitted with a stirrer, a reflux condenser and a dropping funnel was placed 50 g of diethyl phthalate. The temperature was then elevated to 200° C., and, with stirring, 95 g of β-hydroxycyclopentyl-t-butylperoxide (2) was slowly added through the dropping funnel for 1.5 hours.

After heating and stirring for 2 hours, the reaction solution was cooled and extracted with water. 45 g of glutaraldehydes were obtained.

EXAMPLE 6

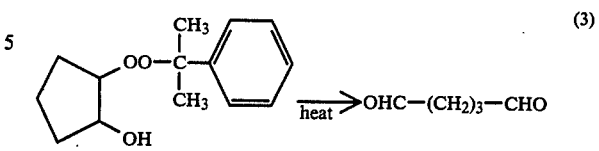

Beta-hydroxycyclopentylcumylperoxide (3) was prepared in the procedure described in Example 3, and it was then thermally cracked as follows:

In a 200 cc, glass reactor fitted with a stirrer, a reflux condenser and a dropping funnel was placed 50 g of dodecane. The temperature was then elevated to 160° C., and, with stirring, 59 g of β-hydroxycyclopentyl-cumylperoxide (3) was added through the dropping funnel for one hour.

After heating and stirring at 160° C. for 4 hours, the cracking solution was vacuum distilled. 20 g of glutaraldehydes were obtained.

EXAMPLE 7

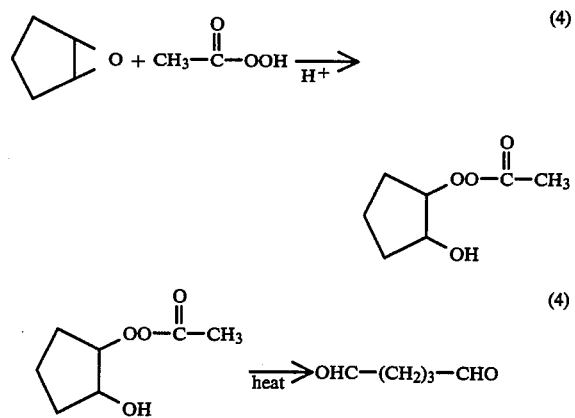

Beta-hydroxycyclopentylacetylperoxide (4) was prepared similarly as in Examples 1 and 2, and it was then thermally cracked as follows:

In a 200 cc, glass reactor fitted with a stirrer, a reflux condenser and a dropping funnel was placed 50 g of trioctyl phosphate. The temperature was then elevated to 120° C., and, with stirring, a solution of 39 g of β-hydroxycyclopentylacetylperoxide (4) and 20 g of trioctyl hosphate was added through the funnel for 1.5 hours.

After heating and stirring at 120° C. for 2 hours, the cracking solution was vacuum distilled. 19 g of glutaraldehydes were obtained.

EXAMPLE 8

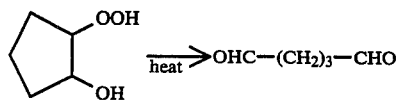

Beta-hydroxycyclopentylhydroperoxide (1) was prepared in the procedure described in Example 1, and it was then thermally cracked as follows:

In a 200 cc, glass reactor fitted with a stirrer, a reflux condenser and a dropping funnel was placed 30 g of water. The temperature was elevated to 95° C., and then a solution of 31 g of β-hydroxycyclopentylhydroperoxide (1) and 35 g of water was added through the dropping funnel for one hour.

After heating for 4 hours at 95° C. with stirring, the cracking solution was vacuum distilled. 16 g of glutaraldehydes were obtained.

EXAMPLE 9

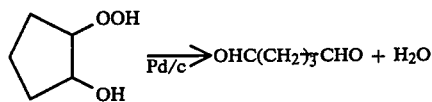
(1)

A dimethyl phthalate solution of β-hydroxycyclopentylhydroperoxide (1) prepared as in Example 1 was catalytically cracked as follows:

In a 200 cc, glass reactor fitted with a stirrer, a reflux condenser and a dropping funnel were placed 7.5 g of Pd/C (with 5% Pd) powders and 20 g of dimethyl phthalate. The temperature was then elevated to 80° C., and, with stirring, 67 g of a dimethyl phthalate solution containing 20.5 g of β-hydroxycyclopentylhydroperoxide (1) was added through the dropping funnel for 2 hours.

After the addition was completed, heating was continued for 4.5 hours with stirring, and the reaction solution was gas chromatographed on the column of FFAP. It was found that the reaction solution contains 15% by weight of glutaraldehydes. No remaining peroxide in the reaction solution was confirmed by the iodometry. The reaction solution was then extracted with water to separate glutaraldehydes. Yield 16.0 g.

EXAMPLE 10

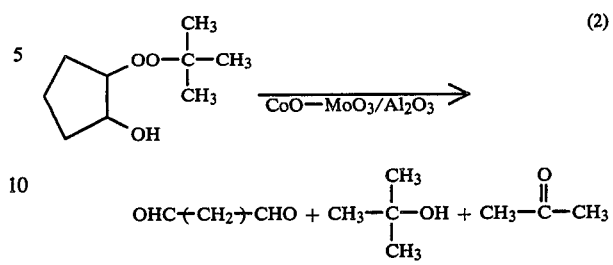

Beta-hydroxycyclopentyl-t-butylperoxide (2) prepared as in Example 2 was catalytically cracked as follows:

In a 200 cc, glass reactor fitted with a stirrer, a reflux condenser and a dropping funnel was placed 3.5 g CoO-MoO$_3$/Al$_2$O$_3$ (with 4% CoO and 12%) powders. The temperature was thereafter elevated to 50° C., and, with stirring, 40 g of β-hydroxycyclopentyl-t-butylperoxide (2) was slowly added through the dropping funnel for 3 hours.

After heating was continued for 2 hours with stirring, the reaction solution was cooled, the catalyst was filtered off and the filtrate was extracted with water to separate glutaraldehydes. Yield 15.4 g.

EXAMPLES 11-28

Different β-hydroxycyclopentylperoxide compounds were prepared as in Example 1 to 3, and were catalytically cracked in the presence of the catalyst.

Results are reported in Table 1.

TABLE 1

| | | | Reaction Conditions | | Glutaroldehyde | |
|---|---|---|---|---|---|---|
| Composition of Starting Materials | | | | | | |
| Ex | Cyclopentylperoxide compound (g) | Catalyst (g) | Solvent (g) | Temp. (°C.) | Time (hr) | Yield (g) | Yield (%) |
| 11 | 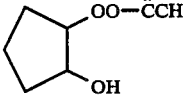 (41) | Cu(CH$_3$COO)$_2$ (0.45) | dodecane (80) | 50 | 4.5 | 16.9 | 66 |
| 12 | 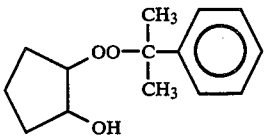 (56) | Pd Black (0.9) | trioctyl phosphate (80) | 90 | 4.0 | 18.0 | 76 |
| 13 | 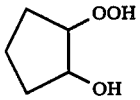 (22) | Pt black (0.8) | anisole (90) | 78 | 6.1 | 16.9 | 91 |
| 14 | 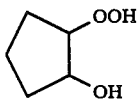 (22) | CrCl$_3$ (0.8) | isoamyl acetate (100) | 60 | 3.0 | 16.5 | 65 |

TABLE 1-continued

| | Composition of Starting Materials | | | Reaction Conditions | | Glutarol dehyde | |
|---|---|---|---|---|---|---|---|
| Ex | Cyclopentylperoxide compound (g) | Catalyst (g) | Solvent (g) | Temp. (°C.) | Time (hr) | Yield (g) | Yield (%) |
| 15 | cyclopentyl-OO-CH(CH₃)-C₆H₅ with OH (58) | H₂WO₄ (1.2) | ethyl benzoate (90) | 90 | 5.3 | 17.8 | 68 |
| 16 | cyclopentyl-OO-C(CH₂CH₃)(CH₃)-OOH with OH (65) | VOCl₃ (0.9) | ethyl acetate (65) | 80 | 4.2 | 21.1 | 67 |
| 17 | cyclopentyl-OO-C(=O)-(2,4-dichlorophenyl) with OH (41) | FeCl₃ (0.5) | dimethyl phthalate (50) | 55 | 5.0 | 8.9 | 63 |
| 18 | cyclopentyl-OOH with OH (26) | Al(C₅H₇O₂)₃ (1.4) | butyl acetate (95) | 60 | 4.5 | 16.1 | 73 |
| 19 | cyclopentyl-OOH with OH (30) | Rh(C₅H₇O₂)₃ (1.8) | ethyl benzoate (100) | 83 | 5.0 | 22.9 | 90 |
| 20 | cyclopentyl-OO-C(CH₃)₃ with OH (37) | TiO(C₅H₇O₂)₂ (1.1) | isoamyl acetate (95) | 88 | 6.3 | 13.2 | 62 |
| 21 | cyclopentyl-OOH with OH (25) | ZrCl₄ (1.2) | ethyl acetate (100) | 75 | 4.4 | 16.0 | 76 |
| 22 | cyclopentyl-OOH with OH (24) | SnCl₄ (1.3) | dimethyl phthalate (105) | 55 | 3.8 | 13.9 | 68 |

TABLE 1-continued

| Ex | Cyclopentylperoxide compound (g) | Catalyst (g) | Solvent (g) | Temp. (°C.) | Time (hr) | Yield (g) | Yield (%) |
|---|---|---|---|---|---|---|---|
| 23 | 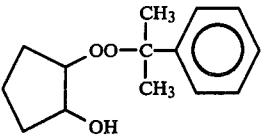 (52) | Pb(CH$_3$COO)$_4$ (2.7) | isopropyl acetate (80) | 95 | 7.1 | 13.9 | 63 |
| 24 | 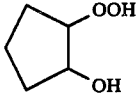 (25) | OsO$_4$ (1.2) | dimethyl phthalate (110) | 78 | 5.0 | 18.9 | 90 |
| 25 | 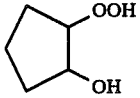 (22) | Irblack (0.9) | ethyl benzoate (100) | 80 | 4.0 | 17.5 | 94 |
| 26 | 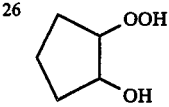 (23) | Pd/Al$_2$O$_3$ (with 1.0% Pd) (13) | dimethyl phthalate (82) | 88 | 7.0 | 17.6 | 90 |
| 27 | 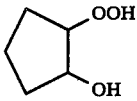 (26) | H$_3$PO$_3$ (1.2) | dibutyl ether (100) | 95 | 10.5 | 15.4 | 70 |
| 28 | 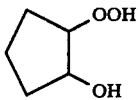 (22) | RuCl$_3$·H$_2$O (1.1) | ethyl benzoate (95) | 75 | 4.0 | 14.5 | 78 |

Column headers: Composition of Starting Materials; Reaction Conditions; Glutaroldehyde Yield

EXAMPLE 29

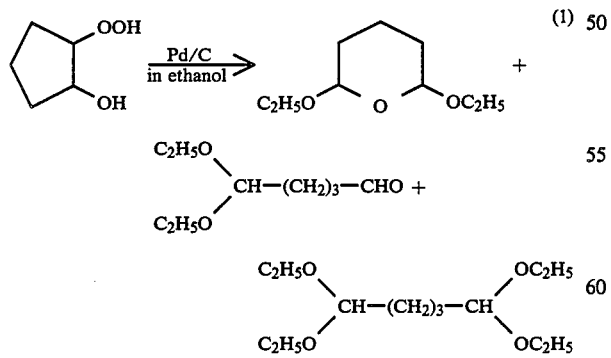

Beta-hydroxycyclo-pentylhydroperoxide (1) prepared as in Example 1 was reacted with ethanol to form acetals:

In a 300 cc, 3-necked flask fitted with a stirrer, a reflux condenser and a dropping funnel were placed 7.0 g of Pd/C (with 5% Pd) powders and 45 g of ethanol. The mixture was heated, and, under boiling conditions of ethanol, 21.0 g of β-hydroxycyclopentylhydroperoxide (1) solution diluted with 70 g of ethanol was dropwise added through the funnel for one hour.

After the addition was completed, the reaction was further continued at the boiling temperature for 6 hours. The reaction solution was gas chromatographed on the column of FFAP. It was found that 10.6 g of cis- and trans- 2,6-diethoxytetrahydropyrane, 6.7 g of 5,5-diethoxypentanol and 15.1 g of 1,1,5,5-tetraethoxypentane were produced. Yield of acetals was 90%. No unreacted peroxide in the reaction solution was confirmed with the iodometry.

EXAMPLE 30

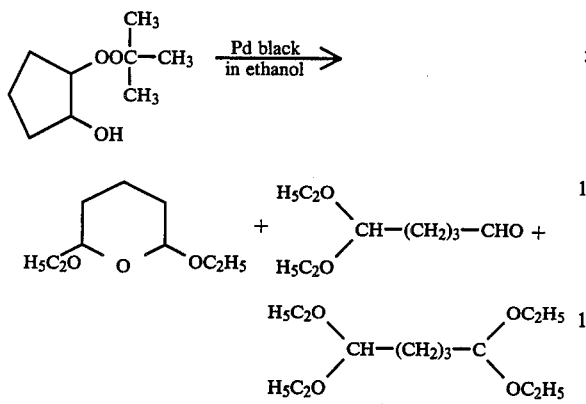

Beta-hydroxycyclopentyl-t-butyl-peroxide (2) prepared as in Example 2 was reacted with ethanol in the presence of palladium black catalyst in the manner similar to that of Example 29 described above: Namely, in the flask used in Example 1 were placed 0.89 g of palladium black and 60 g of ethanol. At the boiling temperature of ethanol, a solution of 39.5 g of β-hydroxycyclopentyl-t-butylperoxide (2) in 60 g of ethanol was dropwise added through the dropping funnel for 0.5 hour.

After the addition was completed, heating was continued with stirring for 8 hours. The reaction solution was distilled to remove excess ethanol, and then fractionally distilled in a rotary band fractionating tower. 9.8 g of cis-2,5-diethoxytetrahydropyrane was fractioned at 51° C./3 mmHg(b.p.), 2.9 g of trans-2,5-diethoxytetrahydropyrane at 65° C./2 mmHg (b.p.), 9.1 g of 5,5-diethoxypentanol at 81° C./2 mmHg (b.p.) and 19.0 g of 1,1,5,5-tetraethoxypentane at 97° C./2 mmHg. Yield of acetals was 89%.

EXAMPLE 31

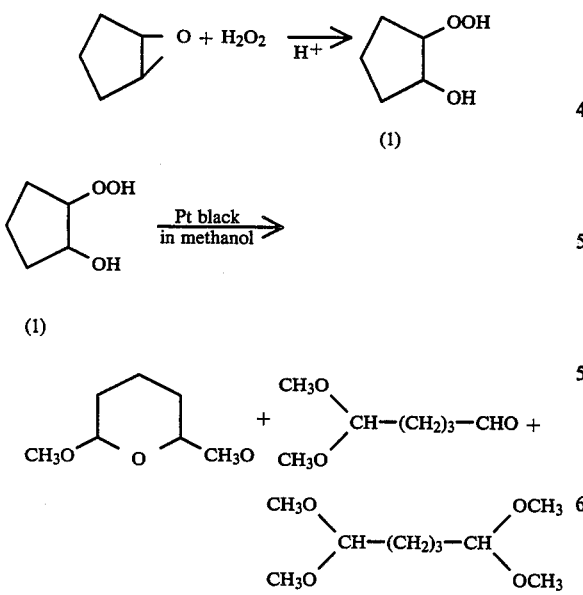

Cyclopenteneoxide and hydrogen peroxide were first reacted in the presence of Amberlist 15 as the catalyst in the same manner as in Example 1. After completion of the reaction, the catalyst was filtered off. A dimethyl phthalate solution containing 23% by weight of β-hydroxycyclopentylhydroperoxide was obtained.

Second, the resulting reaction solution was reacted with methanol as follows (β-hydroxycyclopentylhydroperoxide was not separated from the reaction solution):

In a 500 cc, 3-necked flask fitted with a stirrer, a reflux condenser and a dropping funnel were placed 0.90 g of platinum black and 120 g of methanol, and heated. With boiling of ethanol, 100 g of the above-described reaction solution was added through the dropping funnel for one hour. After the addition was completed, heating was continued with stirring for further 8 hours, and the reaction solution was gas chromatographed. It was found that 10.2 g of 2,6-dimethoxytetrahydropyrane, 5.1 g of 5,5-dimethoxypentanol and 11.5 g of 1,1,5,5-tetramethoxypentane were produced. Yield of these acetals was 85%.

EXAMPLE 32

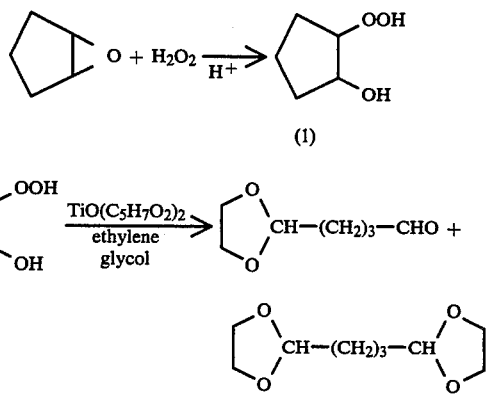

Beta-hydroxycyclopentylhydroperoxide (1) prepared as in Example 1 was reacted with ethylene glycol as follows:

In a 300 cc, 3-necked flask fitted with a stirrer, a reflux condenser and a dropping funnel were placed 1.12 g of TiO($C_5H_7O_2$)$_2$ and 50 g of ethylene glycol, and heated. Subsequently, a solution of 30 g of β-hydroxycyclopentylhydroperoxide (1) and 90 g of ethylene glycol was dropwise added through the funnel for one hour.

After the addition was completed, the reaction was continued at 90° C. for further 4.5 hours. After completion of the reaction, the reaction product was separated with preparative liquid chromatography to yield 5.6 g of 4-(2',5'-dioxacyclopentyl)butyl-1-al and 23.7 g of 1,3-bis(2',5'-dioxacyclopentyl)propane. Yield of these acetals was 65%.

EXAMPLES 33–51

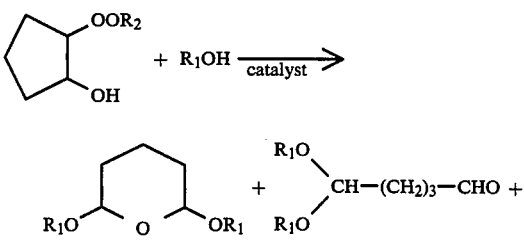

-continued

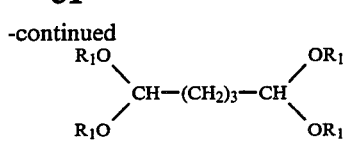

Different β-hydroxycyclopentylperoxide compounds were prepared in the manner similar to those of Examples 1 to 3, and were converted in the presence of the catalyst to acetals.

Results are reported in Table 2.

TABLE 2

| | Composition of Starting Materials | | | | Reaction Conditions | | Acetal[1] | | | |
|---|---|---|---|---|---|---|---|---|---|---|
| | Cyclopentylperoxide | | | | | | | | | |
| Ex | Compound (g) | Catalyst (g) | Alcohol (g) | Solvent[2] (g) | Temp. (°C.) | Time[3] (hr) | A (g) | B (g) | C (g) | Yield (%) |
| 33 | [cyclopentyl-OOH/OH] (20.5) | Ad/Al₂O₃ (with 1% Pd) (13.1) | methanol (150) | none | 65 | 10 | 10.5 | 3.2 | 12.1 | 90 |
| 34 | [cyclopentyl-OOH/OH] (22.0) | Ni(C₅H₇O₂)₂ (0.95) | methanol (100) | none | 65 | 11 | 11.5 | 3.0 | 11.2 | 85 |
| 35 | [cyclopentyl-OOH/OH] (30.0) | CoO—MoO₃/Al₂O₃ (with 4% CoO and 12% MoO₃) (3.41) | ethanol (120) | none | 70 | 5 | 13.6 | 6.8 | 14.3 | 69 |
| 36 | [cyclopentyl-OO-CH(CH₃)-Ph/OH] (56.0) | H₂WO₄ (2.25) | methanol (120) | none | 65 | 12 | 14.5 | 4.3 | 13.4 | 79 |
| 37 | [cyclopentyl-OOH/OH] (26.0) | Rh(C₅H₇O₂)₃ (2.03) | isopropyl alcohol (130) | none | 82 | 8 | 15.4 | 10.7 | 6.9 | 69 |
| 38 | [cyclopentyl-OOH/OH] (25.1) | Fe₂O₃ (0.60) | ethanol (110) | dimethyl phthalate (30) | 78 | 8 | 15.0 | 2.7 | 13.6 | 74 |
| 39 | [cyclopentyl-OOH/OH] (24.0) | Sn(OCOCH₃)₂ (1.31) | ethanol (110) | none | 78 | 10 | 11.0 | 4.1 | 12.9 | 68 |

TABLE 2-continued

| | Composition of Starting Materials | | | | Reaction Conditions | | Acetal[1] | | | |
|---|---|---|---|---|---|---|---|---|---|---|
| | Cyclopentylperoxide Compound | Catalyst | Alcohol | Solvent[2] | Temp. | Time[3] | A | B | C | Yield |
| Ex | (g) | (g) | (g) | (g) | (°C.) | (hr) | (g) | (g) | (g) | (%) |
| 40 | cyclopentyl-OOH, -OH (25.0) | OsO$_4$ (1.20) | ethanol (130) | none | 78 | 11 | 14.6 | 3.6 | 14.8 | 77 |
| 41 | cyclopentyl-OOH, -OH (22.0) | Irblack (2.0) | cyclo-pentanol (180) | none | 92 | 6 | 19.4 | 3.9 | 4.2 | 55 |
| 42 | cyclopentyl-OOH, -OH (23.9) | Ag$_2$O (0.93) | ethanol (110) | none | 78 | 7 | 15.1 | 2.7 | 10.6 | 72 |
| 43 | cyclopentyl-OOH, -OH (25.0) | PbO$_2$ (0.9) | ethanol (110) | none | 78 | 8 | 10.0 | 5.0 | 12.1 | 64 |
| 44 | cyclopentyl-OOH, -OH (20.5) | CrCl$_3$ (0.83) | ethanol (100) | n-hexane (80) | 78 | 5 | 10.0 | 3.9 | 9.8 | 69 |
| 45 | cyclopentyl-OOH, -OH (29.0) | VOCl$_3$ (1.0) | methanol (120) | none | 65 | 10 | 13.9 | 23 | 13.1 | 73 |
| 46 | cyclopentyl-OOH, -OH (27.0) | Pd/Al$_2$O$_3$ (with 1% Pd) (10.9) | isopropyl alcohol (130) | none | 82 | 9 | 24.4 | 9.2 | 10.0 | 87 |
| 47 | cyclopentyl-OOH, -OH (20.0) | Cu(OCOCH$_3$)$_2$ (0.46) | ethanol (110) | none | 78 | 6 | 8.9 | 2.5 | 12.0 | 67 |

TABLE 2-continued

| | Composition of Starting Materials | | | | Reaction Conditions | | Acetal[1] | | | |
|---|---|---|---|---|---|---|---|---|---|---|
| | Cyclopentylperoxide | | | | | | | | | |
| Ex | Compound (g) | Catalyst (g) | Alcohol (g) | Solvent[2] (g) | Temp. (°C.) | Time[3] (hr) | A (g) | B (g) | C (g) | Yield (%) |
| 48 | 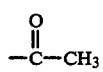 (22.8) | Al(C$_5$H$_7$O$_2$)$_3$ (1.52) | ethanol (115) | none | 78 | 8 | 11.2 | 2.8 | 12.1 | 67 |
| 49 | (same structure) (21.0) | H$_3$BO$_3$ (1.23) | methanol (100) | ethyl benzoate (50) | 65 | 15 | 13.2 | 1.1 | 10.1 | 85 |
| 50 | (same structure) (22.0) | Mn(C$_5$H$_7$O$_2$)$_3$ (1.8) | ethanol (140) | none | 78 | 7 | 10.1 | 5.0 | 11.4 | 71 |
| 51 | (same structure) (20.3) | ZrCl$_4$ (1.3) | ethanol (135) | none | 78 | 9 | 10.8 | 3.6 | 13.6 | 80 |

Acetal[1]

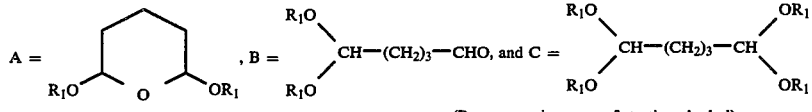

($R_1$ = organic group of starting alcohol)

Solvent[2] . . . solvent other than starting alcohol
Time[3] . . . including addition time of cyclopentylperoxide compound.

What is claimed is:

1. Beta-hydroxycyclopentylperoxide compound of the formula:

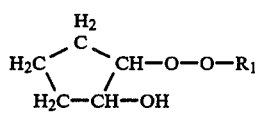

wherein $R_1$ represents a hydrogen atom, a hydrocarbon of 1 to 9 carbon atoms, or a —OH, =O, —Cl and —OOH substitued hydrocarbon of 1 to 9 carbon atoms.

2. The compound of claim 1, in which said compound is β-hydroxycyclopentylhydroperoxide.

3. The compound of claim 1, in which said compound is β-hydroxycyclopentyl-tert.-butylperoxide.

4. The compound of claim 1, in which said compound is β-hydroxycyclopentylcumylperoxide.

5. The compound of claim 1 in which $R_1$ is $$-\overset{O}{\underset{\|}{C}}-CH_3$$

6. The compound of claim 1 in which $R_1$ is

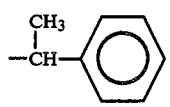

7. The compound of claim 1 in which $R_1$ is $$-\overset{C_2H_5}{\underset{CH_3}{\overset{|}{\underset{|}{C}}}}-OOH$$

8. The compound of claim 1 in which $R_1$ is

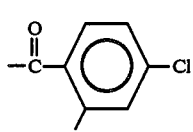

9. The compound of claim 1 in which $R_1$ is selected from the group consisting of

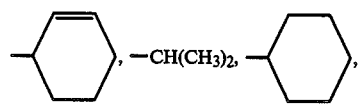
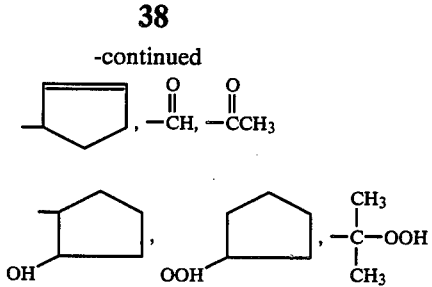
* * * * *